(12) United States Patent  
Sevick-Muraca et al.

(10) Patent No.: US 7,599,732 B2  
(45) Date of Patent: Oct. 6, 2009

(54) METHOD AND SYSTEM FOR NEAR-INFRARED FLUORESCENCE CONTRAST-ENHANCED IMAGING WITH AREA ILLUMINATION AND AREA DETECTION

(75) Inventors: Eva M. Sevick-Muraca, Edinburg, TX (US); Alan B. Thompson, Hillsboro, OR (US); Roy Ranadhir, Edinburg, TX (US)

(73) Assignee: The Texas A&M University System, College Station, TX (US)

( * ) Notice: Subject to any disclaimer, the term of this patent is extended or adjusted under 35 U.S.C. 154(b) by 672 days.

(21) Appl. No.: 10/872,333

(22) Filed: Jun. 18, 2004

(65) Prior Publication Data

US 2005/0085732 A1    Apr. 21, 2005

Related U.S. Application Data

(60) Provisional application No. 60/480,526, filed on Jun. 20, 2003.

(51) Int. Cl.  
*A61B 5/00*  (2006.01)

(52) U.S. Cl. ............................ 600/476; 60/473; 60/310; 356/317; 356/318; 356/301

(58) Field of Classification Search .................. 600/473, 600/476, 310; 356/317, 318, 301  
See application file for complete search history.

(56) References Cited

U.S. PATENT DOCUMENTS 4,541,438 A    9/1985   Parker et al. ................ 128/664
5,022,757 A    6/1991   Modell ........................ 128/664
5,070,455 A    12/1991  Singer et al. ........... 364/413.19
5,119,815 A    6/1992   Chance ........................ 128/633
5,142,372 A    8/1992   Alfano et al. ................ 128/664
5,190,729 A    3/1993   Hauenstein et al. ........... 422/91
5,208,651 A    5/1993   Buican ........................ 356/346
5,213,105 A    5/1993   Grafton et al. ............. 128/664
5,340,991 A    8/1994   Fransen et al. .............. 128/664

(Continued)

FOREIGN PATENT DOCUMENTS

EP          0 959 341         11/1999

(Continued)

OTHER PUBLICATIONS

Reynolds, et al., "*Imaging of Spontaneous Canine Mammary Tumors Using Fluorescent Contrast Agents*", Photochemistry and Photobiology, 1999: 70(1): 87-94 (XP-001063376), Apr. 14, 1999.

(Continued)

*Primary Examiner*—Brian Casler  
*Assistant Examiner*—Baisakhi Roy  
(74) *Attorney, Agent, or Firm*—Baker Botts L.L.P.

(57) ABSTRACT

According to one embodiment of the invention, a method for biomedical imaging includes directing time-varying excitation light at a surface area of a light scattering material, the material comprising a fluorescent target. Time-varying emission light from the fluorescent target is detected, substantially at a two-dimensional sensor surface, in response to the time-varying excitation light stimulating the fluorescent target. The time-varying emission light is filtered to reject excitation light re-emitted from the material. A three-dimensional image of the fluorescent target is generated based on the detection substantially at the sensor surface.

21 Claims, 4 Drawing Sheets

U.S. PATENT DOCUMENTS

| | | | |
|---|---|---|---|
| 5,353,799 A | 10/1994 | Chance | 128/664 |
| 5,413,098 A | 5/1995 | Benaron | 128/633 |
| 5,421,337 A | 6/1995 | Richards-Kortum et al. | 128/633 |
| 5,421,339 A | 6/1995 | Ramanujam et al. | 128/665 |
| 5,424,843 A | 6/1995 | Tromberg et al. | 356/442 |
| 5,441,054 A | 8/1995 | Tsuchiya | 128/665 |
| 5,452,723 A | 9/1995 | Wu et al. | 128/665 |
| 5,485,530 A | 1/1996 | Lakowicz et al. | 382/191 |
| 5,504,337 A | 4/1996 | Lakowicz et al. | 250/461.2 |
| 5,507,287 A | 4/1996 | Palcic et al. | 128/633 |
| 5,579,773 A | 12/1996 | Vo-Dinh et al. | 128/665 |
| 5,582,168 A | 12/1996 | Samuels et al. | 128/633 |
| 5,590,660 A | 1/1997 | MacAulay et al. | 128/664 |
| 5,624,847 A | 4/1997 | Lakowicz et al. | 436/68 |
| 5,628,310 A | 5/1997 | Rao et al. | 128/633 |
| 5,647,368 A | 7/1997 | Zeng et al. | 128/665 |
| 5,692,504 A | 12/1997 | Essenpreis et al. | 600/316 |
| 5,699,798 A | 12/1997 | Hochman et al. | 600/420 |
| 5,736,410 A | 4/1998 | Zarling et al. | 436/172 |
| 5,759,767 A | 6/1998 | Lakowicz et al. | 435/4 |
| 5,792,049 A | 8/1998 | Eppstein et al. | 600/306 |
| 5,818,583 A | 10/1998 | Sevick-Muraca et al. | 600/476 |
| 5,832,931 A | 11/1998 | Wachter et al. | 128/898 |
| 5,860,421 A | 1/1999 | Eppstein et al. | 128/660.06 |
| 5,865,754 A * | 2/1999 | Sevick-Muraca et al. | 600/476 |
| 5,891,656 A | 4/1999 | Zarling et al. | 435/7.92 |
| 5,917,190 A | 6/1999 | Yodh et al. | 250/458.1 |
| 5,919,140 A | 7/1999 | Perelman et al. | 600/476 |
| 5,928,627 A | 7/1999 | Kiefer et al. | 424/9.6 |
| 5,949,077 A | 9/1999 | Alfano et al. | 250/459.1 |
| 6,032,070 A * | 2/2000 | Flock et al. | 600/473 |
| 6,070,583 A | 6/2000 | Perelman et al. | 128/665 |
| 6,104,939 A * | 8/2000 | Groner et al. | 600/322 |
| 6,216,540 B1 | 4/2001 | Nelson et al. | 73/633 |
| 6,271,522 B1 | 8/2001 | Lindermeir et al. | 250/341.1 |
| 6,272,374 B1 * | 8/2001 | Flock et al. | 600/473 |
| 6,304,771 B1 | 10/2001 | Yodh et al. | 600/476 |
| 6,321,111 B1 | 11/2001 | Perelman et al. | 600/477 |
| 6,480,276 B1 | 11/2002 | Jiang | 356/336 |
| 6,640,124 B2 * | 10/2003 | Elsner et al. | 600/407 |
| 6,671,540 B1 | 12/2003 | Hochman | 600/431 |
| 6,771,370 B2 | 8/2004 | Sevick-Muraca et al. | 356/336 |
| 6,930,777 B1 | 8/2005 | Sevick-Muraca et al. | 356/336 |
| 6,965,431 B2 * | 11/2005 | Vo-Dinh et al. | 356/301 |
| 7,054,002 B1 | 5/2006 | Sevick-Muraca et al. | 356/317 |
| 7,187,441 B1 | 3/2007 | Sevick-Muraca et al. | 356/336 |
| 7,268,873 B2 | 9/2007 | Sevick-Muraca et al. | 356/336 |
| 7,328,059 B2 | 2/2008 | Sevick-Muraca et al. | 600/473 |
| 2001/0027273 A1* | 10/2001 | Flock et al. | 600/473 |
| 2002/0072677 A1* | 6/2002 | Sevick-Muraca et al. | 600/473 |
| 2008/0175790 A1 | 7/2008 | Sevick-Muraca et al. | 424/9.6 |

FOREIGN PATENT DOCUMENTS

| | | |
|---|---|---|
| GB | 2311366 A | 3/1996 |
| JP | 2-268256 | 1/1990 |
| JP | H07-507472 | 8/1995 |
| WO | WO 95/12132 | 5/1995 |
| WO | WO 97/08538 | 3/1997 |
| WO | WO 99/49312 | 3/1999 |
| WO | WO 00/22414 | 10/1999 |
| WO | WO 01/22063 | 9/2000 |
| WO | WO 02/41760 A2 | 5/2002 |

OTHER PUBLICATIONS

Gurfinkel, et al., "Pharmacokinetcs of ICG and HPPH-car for the Detection of Normal and Tumor Tissue Using Fluorescence, Near-infrared Reflectance Imaging: A Case Study", Photochemistry and Photobiology, 2000: 72(1): 94-102 (XP-001030699), Apr. 28, 2000.

Thompson, et al., "Near-infrared fluorescence contrast-enhanced imaging with intensified charge-coupled device homodyne detection: measurement precision and accuracy", Journal of Biomedical Optics, 2003: 8(1): 111-120 (XP-002301882), Jan. 2003.

Thompson, et al., "Near-infrared fluorescence contrast-enhanced imaging with area illumination and area detection: the forward imaging problem", Applied Optics, 2003: 42(19): 4125-4136 (XP-002301883), Jul. 1, 2003.

Notification of Transmittal of the International Search Report and the Written Opinion of the International Searching Authority for International Application No. PCT/US2004/019792, filed Jun. 18, 2004 (14 pages), Nov. 8, 2004.

Sevick-Muraca et al., Method and System for Detecting Sentinel Lymph Nodes, U.S. Appl. No. 10/618,194, filed Jul. 11, 2003.

Sevick-Muraca et al., Method for Characterizing Particles in Suspension from Frequency Domain Photon Migration Measurements, U.S. Appl. No. 11/204,844, filed Aug. 16, 2005 (now abandoned).

PCT patent application re PCT/US99/23709 filed Oct. 9, 1999, Characterization of Luminescence in a Scattering Medium, Sevick-Muraca, et al.

Communication dated Apr. 3, 2008 from the US Patent and Trademark Office in re U.S. Appl. No. 10/618,194, filed Jul. 11, 2003, by Sevick-Muraca.

Adams et al., Mudpack: Multigrid portable Fortran software for the efficient solution of linear elliptic partial differential equations, Applied Mathematics and Computation 34:113-146 (1989), © Elsevier Science Publishing Co., Inc. 1989.

Anderson, R. Rox, MD, Polarized light examination and photography of the Skin, Arch Dermat—vol. 127, Jul. 1991, pp. 1000-1005.

Banerjee et al., Assessment of $S(0,\varphi)$ from multiply scattered light, Journal of Chemical Physics, vol. III, No. 20, Nov. 22, 1999, © 1999 American Institute of Physics, pp. 9133-9136.

Banerjee et al., Probing static structure of colloid-polymer suspensions with multiply scattered light, Journal of Colloid and Interface Science 209, 142-153 (1999).

Cerussi et al., Experimental verification of a theory for the time-resolved fluorescence spectroscopy of thick tissues, Applied Optics, vol. 36, No. 1, Jan. 1, 1997, pp. 116-124.

Chance et al., Phase measurement of light absorption and scatter in human tissue, Review of Scientific Instruments, vol. 69, No. 10, Oct. 1998, American Institute of Physics, pp. 3457-3481.

Chernomordik et al., Inverse method 3-D reconstruction of localized in vivo fluorescence-application to Sjøgren syndrome, IEEE Journal of Selected Topics in Quantum Electronics, vol. 5, No. 4, Jul./Aug. 1999, pp. 930-935.

Demos et al., Optical polarization imaging, Applied Optics, vol. 36, No. 1, Jan. 1, 1997, pp. 150-155.

Dimitratos et al., Control of emulsion polymerization reactors, AIChE Journal, Dec. 1994, vol. 40, No. 12, pp. 1993-2021.

Durian, Influence of boundary reflection and refraction on diffusive photon transport, Physical Review E, vol. 50, No. 2, Aug. 1994, © 1994 The American Physical Society, pp. 857-866.

Eliçabe et al., Latex particle size distribution from turbidimetric measurements, Combining regularization and generalized cross-validation techniques, © 1990 American Chemical Society, pp. 83-104.

Eppstein et al., Biomedical optical tomography using dynamic parameterization and Bayesian conditioning on photon migration measurements, Applied Optics, vol. 38, No. 10, Apr. 1, 1999, pp. 2138-2150.

Eppstein et al., 3D, Bayesian image reconstruction from sparse and noisy data sets: Near-infrared fluorescence tomography, PNAS, Jul. 23, 2002, vol. 99, No. 15, pp. 9619-9624.

Eppstein et al., 3D, Bayesian optical imaging reconstruction with domain decomposition, IEEE Transactions on Medical Imaging, vol. 20, No. 3, Mar. 2001, pp. 147-163.

Fantini et al., Quantitative determination of the absorption spectra of chromophores in strongly scattering media: a light-emitted-diode based technique, Applied Optics, vol. 33, No. 22, Aug. 1, 1994, pp. 5204-5213.

Farrell et al., Nonlinear controller for batch crystallization: Development and experimental demonstration, AIChE Journal, Oct. 1995, vol. 41, No. 10, pp. 2318-2321, 1994.

Fishkin et al., *Frequency-domain method for measuring spectral properties in multiple-scattering media: methemoglobin absorption spectrum in a tissuelike phantom*, Mar. 1, 1995, vol. 34, No. 7, Applied Optics, pp. 1143-1155.

Fishkin et al., *Frequency-domain photon migration measurements of normal and malignant tissue optical properties in a human subject*, Applied Optics, vol. 36, No. 1, Jan. 1, 1997, pp. 10-20.

Fishkin et al., *Propagation of photon-density waves in strongly scattering media containing an absorbing semi-infinite plane bounded by a straight edge*, vol. 10, No. 1, Jan. 1993, pp. 127-140.

Fraden et al., *Multiple light scattering from concentrated, interacting suspensions*, © 1990 The American Physical Society, vol. 65, No. 4, Jul. 23, 1990, pp. 512-515.

Garcia-Rubio et al., *Refractive index effects on the absorption spectra of macromolecules*, © 1992 American Chemical Society, Macromolecules 1992, 25, 2608-2613.

Gerken et al., *High-precision frequency-domain measurements of the optical properties of turbid media*, © 1999 Optical Society of America, Optics Letters, vol. 24, No. 14, Jul. 15, 1999, pp. 930-932.

Godavarty et al., *Influence of the refractive index-mismatch at the boundaries measured in fluorescence-enhanced frequency-domain photon migration imaging*, Jul. 29, 2002, vol. 10, No. 15, Optics Express, pp. 653-662.

Graaff et al., *Reduced light-scattering properties for mixtures of spherical particles: a simple approximation derived from Mie calculations*, Applied Optics, vol. 31, No. 10, Apr. 1, 1992, pp. 1370-1376.

Gratton et al., *A continuously variable frequency cross-correlation phase fluorometer with picosecond resolution*, Biophys. J. © Biophysical Society, vol. 44, Dec. 1983, pp. 315-324.

Gratton et al., *The possibility of a near-infrared optical imaging system using frequency domain methods*, Mind Brain Imaging Program, Aug. 5-10, 1990 Hamamatsu, Japan, pp. 183-189.

Gurfinkel et al., *Pharmacokinetics of ICG and HPPH-car for the detection of normal and tumor tissue using fluorescence, near-infrared reflectance imaging: a case study*, Photochemistry and Photobiology, 2000, 72, pp. 94-102.

Haskell et al., *Boundary conditions for the diffusion equation in radiative transfer*, © 1994 Optical Society of America, vol. 11, No. 10, Oct. 1994, pp. 2727-2741.

Hawrysz et al., *Developments toward diagnostic breast cancer imaging using near-infrared optical measurements and fluorescent contrast agents*, Neoplasia, vol. 2, No. 5, Sep.-Oct. 2000, pp. 388-417.

Hawrysz et al., *Error consideration in contrast-enhanced three-dimensional optical tomography*, Optics Letters, vol. 26, No. 10, May 15, 2001, pp. 704-706.

Houston et al., *Sensitivity and depth penetration of continuous wave versus frequency-domain photon migration near-infrared fluorescence contrast-enhanced imaging*, Photochemistry and Photobiology, 2003, 77(4): 420-430.

Hull et al., *Localization of luminescent inhomogeneities in turbid media with spatially resolved measurements of cw diffuse luminescence emittance*, May 1, 1998, vol. 37, No. 13, Applied Optics, pp. 2755-2765.

Hutchinson et al., *Fluorescence-lifetime determination in tissues or other scattering media from measurement of excitation and emission kinetics*, May 1, 1996, vol. 35, No. 13, Applied Optics, pp. 2325-2332.

Isayev et al., *Study of thermophysical properties of a metal-hydrogen system*, Int. J. Hydrogen Energy, vol. 21, No. 11/12, pp. 1129-1132, © 1996 International Association for Hydrogen Energy.

Ishimaru et al., *Optical sensing of particle size distribution by neural network technique*, Department of Electrical Engineering, University of Washington, Seattle, Washington 98195, CH2825-8/90/0000—pp. 2129-2131.

Jacques et al., *Imaging superficial tissues with polarized light*, Lasers in Surgery and Medicine 26:119-129, © 2000 Wiley-Liss, Inc.

Jager et al., *On-line particle size measurement in dense slurries*, Power Technology, 62 (1990) pp. 155-162, © Elsevier Sequoia/Printed in The Netherlands.

Jiang et al., *Optical image reconstruction using frequency-domain data: simulations and experiments*, Reprinted from Journal of the Optical Society of America, © 1996, pp. 253-266.

Kienle et al., *Spatially resolved absolute diffuse reflectance measurements for noninvasive determination of the optical scattering and absorption coefficients of biological tissue*, Applied Optics, vol. 35, No. 13, May 1, 1996, pp. 2304-2314.

Lee et al., *Three-dimensional fluorescence enhanced optical tomography using referenced frequency-domain photon migration measurements at emission and excitation wavelengths*, vol. 19, No. 4, Apr. 2002, © 2002 Optical Society of America, pp. 759-771.

Li et al., *Fluorescent diffuse photon density waves in homogeneous and heterogeneous turbid media: analytic solutions and applications* Applied Optics, vol. 35, No. 19, Jul. 1, 1996, pp. 3746-3758.

Li et al., *Fluorescent heterogeneities in turbid media: limits for detection, characterization, and comparison with absorption*, Oct. 1, 1998, vol. 37, No. 28, Applied Optics, pp. 6833-6844.

Lischer et al., *Optical fiber measurements of particle concentration in dense suspensions: calibration and simulation*, Applied Optics, vol. 31, No. 24, Aug. 20, 1992, pp. 5106-5113.

Madsen et al., *Determination of the optical properties of the human uterus using frequency-domain photon migration and steady-state techniques*, Phys. Med. Biol. 39 (1994), pp. 1191-1202, printed in the UK © 1994 IOP Publishing Ltd.

Mayer et al., *Measurement of the fluorescence lifetime in scattering media by frequency-domain photon migration*, Applied Optics, vol. 38, No. 22, Aug. 1, 1999, pp. 4930-4938.

Muzzio et al., *Sampling practices in powder blending*, International Journal of Pharmaceutics 155 (1997) pp. 153-178.

Ntziachristos et al., *Charge-coupled-device based scanner for tomography of fluorescent near-infrared probes in turbid media*, Medical Physics, vol. 29, No. 5, pp. 803-809, May 2002 © 2002 American Association of Physics in Medicine, 14 pages.

Ntziachristos et al., *Concurrent MRI and diffuse optical tomography of breast after indocyanine green enhancement*, PNAS Mar. 14, 2000, vol. 97, No. 6, pp. 2767-2772.

Ntziachristos et al., *Experimental three-dimensional fluorescence reconstruction of diffuse media by use of a normalized Born approximation*, Jun. 15, 2001, vol. 26, No. 12, Optics Letters, © 2001 Optical Society of America, pp. 893-895.

Ntziachristos et al., *In vivo tomographic imaging of near-infrared fluorescence probes*, © 2002 Massachusetts Institute of Technology, Molecular Imaging, vol. 1, No. 2, Apr. 2002, pp. 82-88.

O'Leary et al., *Experimental images of heterogeneous turbid media by frequency-domain diffusing-photon tomography*, Optics Letters, vol. 20, No. 5, Mar. 1, 1995, pp. 426-428.

O'Leary et al., *Fluorescence Lifetime imaging in turbid media*, Optics Letters, vol. 21, No. 2, Jan. 15, 1996, pp. 158-160.

Paithankar et al., *Particle size distribution estimation via solution of the inverse problem of multi-wavelength scattering coefficient measurements*, School of Chemical Engineering, Purdue University, West Lafayette, IN 47907, 17 pages.

Pan et al., *Volume of pharmaceutical powders probed by frequency-domain photo migration measurements of multiply scattered light*, Analytical Chemistry, vol. 74, No. 16, Aug. 15, 2002, pp. 4228-4234.

Panda et al., *Generalized B-spline signal processing*, Signal Processing 55 (1996) 1-14, © 1996 Elsevier Science B.V.

Patterson et al., *Applications of time-resolved light scattering measurements to photodynamic therapy dosimetry*, Hamilton Regional Cancer Centre and McMaster University, Canada, 14 pages.

Patterson et al., *Diffusion equation representation of photon migration in tissue*, Hamilton Regional Cancer Center and McMaster University, Canada, 4 pages.

Patterson et al., *Mathematical model for time-resolved and frequency-domain fluorescence spectroscopy in biological tissues*, Apr. 1, 1994, vol. 33, No. 10, Applied Optics, pp. 1963-1974.

Patterson et al., *Time resolved reflectance and transmittance for the non-invasive measurement of tissue optical properties*, Jun. 15, 1989, vol. 28, No. 12, Applied Optics, pp. 2331-2336.

Pham et al., *Broad bandwidth frequency domain instrument for quantitative tissue optical spectroscopy*, Review of Scientific Instruments, vol. 71, No. 6, Jun. 2000, pp. 2500-2513.

Pierce et al., *Particle size measurement in suspensions through frequency-domain photon migration measurements*, School of Chemical Engineering, Purdue University, IN 47907, 11 pgs.

Pogue et al., *Initial assessment of a simple system for frequency domain diffuse optical tomography*, Phys. Med. Biol. 40 (1995) 1709-1729, Printed in the UK, © 1995 IPO Publishing Ltd.

Rajagopalan et al., *Stabilization of the optical tracer agent indocyanine green using noncovalent interactions*, BioOne, vol. 71, Issue 3, Mar. 2000, Photochemistry and Photobiology, Article: pp. 347-350.

Ramanujam et al., *Sources of phase noise in homodyne and heterodyne phase modulation devices used for tissue oximetry studies*, Review of Scientific Instruments, vol. 69, No. 8, Aug. 1998, pp. 3042-3054, © 1998 American Institute of Physics.

Rawlings et al., *Model identification and control of solution crystallization processes: A review*, Ind. Eng. Chem. Res. 1993, vol. 32, No. 7, pp. 1275-1296.

Reynolds et al., *Multpixel techniques for frequency-domain photon migration imaging*, Biotechnol. Prog. 1997, 13, 669-680, © 1997 American Chemical Society and American Institute of Chemical Engineers.

Richter et al., *Characterization of concentrated colloidal suspension using time-dependent photon migration measurements*, Colloids and Surfaces, A Physicochemical and Engineering Aspects 172 (2000) 163-173.

Richter et al., *Particle sizing using frequency domain photon migration*, Part. Part. Syst. Charact. 15 (1998) 9-15, XP008010433.

Roy et al., *Three-dimensional unconstrained and constrained image-reconstruction techniques applied to fluorescence, frequency-domain photo migration*, Applied Optics, vol. 40, No. 13, May 1, 2001, pp. 2206-2215.

Schnablegger et al., *Sizing of colloidal particles with light scattering: corrections for beginning multiple scattering*, Jun. 20, 1994, vol. 34, No. 18, Applied Optics, pp. 3489-3501.

Sevick et al., *Quantitation of time- and frequency-resolved optical spectra for the determination of Tissue Oxygenation*, Analytical Biochemistry 195, 330-351, © 1991 Academic Press, Inc.

Sevick-Muraca et al., *Fluorescence and absorption contrast mechanisms for biomedical optical imaging using frequency-domain techniques*, Photochemistry and Photobiology, 1997, 66(1), 55-64, © 1997 American Society for Photobiology.

Sevick-Muraca et al., *Measurement of photon migration for particle sizing in optically dense suspensions*, School of Chemistry Engineering, Purdue University, IN 47907 (3 pages).

Sevick-Muraca et al., *33 Near-infrared fluorescence imaging and spectroscopy in random media and tissues*, © 2003 CRC Press LLC, 66 pages.

Sevick-Muraca et al., *Photon-migration measurement of latex size distribution in concentrated suspensions*, AIChE Journal, Mar. 1997, vol. 43, No. 3, pp. 655-664.

Sevick-Muraca et al., *Process monitoring: photon migration measurements in particulate systems*, Fine Particle Society Meeting Aug. 5, 1995 (5 pages).

Shifrin et al., *Spectral attenuation and aerosol particle size distribution*, Applied Optics, vol. 35, No. 12, Apr. 20, 1996, pp. 2114-2124.

Shinde et al., *Frequency-domain photon migration measurements for quantitative Assessment of Power Absorbance: A novel sensor of blend homogeneity*, Journal of Pharmaceutical Sciences, vol. 88, No. 10, Oct. 1999, pp. 959-966.

Shinde et al., *Investigation of static structure factor in dense suspensions by use of multiply scattered light*, Jan. 1, 1999, vol. 38, No. 1, Applied Optics, pp. 197-204.

Sparks et al., *The use of laser backscatter instrumentation for the on-line measurement of the particle size distribution of emulsions*, Part. Part. Syst. Charact. 10 (1993) pp. 279-289.

Sun et al., *Approach for particle sizing in dense polydisperse colloidal suspension using multiple scattered light*, Langmuir 2001, 17, pp. 6142-6147, XP-001126299A, © 2001 American Chemical Society.

Sun et al., *Inversion algorithms for particle sizing with photon migration measurement*, AIChE Journal, Jul. 2001, vol. 47, No. 7, pp. 1487-1498.

Sun et al., *Particle characterization of colloidal suspension at high volume fractions using frequency domain photon migration*, Department of Chemical Engineering, Texas A&M University, College Station, TX 77843-3122, pp. 4/15-12/15.

Sun et al., *Precise analysis of frequency domain photon migration measurement for characterization of concentrated colloidal suspensions*, Review of Scientific Instruments, vol. 73, No. 2, Feb. 2002, pp. 383-393.

Thomas et al., *Fiber optic dynamic light scattering from concentrated dispersions. 3: Particle sizing in concentrates*, Applied Optics, vol. 29, No. 36, Dec. 20, 1990, pp. 5332-5335.

Tromberg et al., *Non-invasive measurements of breast tissue optical properties using frequency-domain photon migration*, Phil. Trans. R. Soc. Land. B (1997), 352, 661-668, © 1997 The Royal Society, pp. 661-668.

Tromberg et al., *Properties of photon density waves in multiple-scattering*, Feb. 1, 1993, vol. 32, No. 4, Applied Optics, pp. 607-616.

Vavra et al., *Application of regression analysis in spectroturbidity size-characterization methods*, Part. Part. Syst. Charact. 12 © VCH Verlagsgesellschaft mbH, D-69469 Weinheim, 1995. pp. 38-41.

Vinogradov et al., *Noninvasive imaging of the distribution in oxygen in tissue in vivo using near-infrared phosphors*, Biophysical Journal, vol. 70, Apr. 1996, pp. 1609-1617.

Wang et al., *A theoretical and experimental study of the total light scattering technique for particle size analysis*, Part. Part. Syst. Charac. 11 (1994) 109-314.

Wang et al., *Retrieved analysis of aerosol-size distribution with simulated extinction measurements at SAGE III wavelengths*, Jan. 20, 1996, vol. 35, No. 3, Applied Optics, pp. 433-440.

Wang et al., *Spherical particle size determination by analytical inversion of the UV-visible-NIR extinction spectrum*, Jan. 1, 1995, vol. 35, No. 1, Applied Optics, pp. 193-197.

Wu et al., *Fluorescence tomographic imaging in turbid media using early-arriving photons and Laplace transforms*, Proc. Natl. Acad. Sci. USA, vol. 94, pp. 8783-8788, Aug. 1997, Medical Sciences.

Wu et al., *Time-resolved multichannel imaging of fluorescent objects embedded in turbid media*, Mar. 1, 1995, vol. 20, No. 5, Optics Letters, pp. 489-491.

PCT Invitation to pay additional fees Mailed Nov. 29, 2002 in re PCT/US02/10433 filed Apr. 3, 2002 (6 pages).

PCT Notification of Transmittal of the International Search Report or the Declaration mailed Jun. 16, 2003 in re PCT/US02/10433 filed Apr. 3, 2002 (10 pages).

Office Action from EPO, Germany, from Formalities Officer, in re Application No. 96 929 029.5-2204 mailed Aug. 19, 2008, Applicant: The Texas A&M University System.

Communication dated Sep. 12, 2003 from the U.S. Patent and Trademark Office in re U.S. Appl. No. 09/870,144, filed May 30, 2001, now U.S. Patent No. 7,328,059, by Sevick-Muraca et al.

Communication dated Nov. 4, 2004 from the U.S. Patent and Trademark Office in re U.S. Appl. No. 09/870,144, filed May 30, 2001, now U.S. Patent No. 7,328,059, by Sevick-Muraca et al.

Communication dated May 4, 2005 from the U.S. Patent and Trademark Office in re U.S. Appl. No. 09/870,144, filed May 30, 2001, now U.S. Patent No. 7,328,059, by Sevick-Muraca et al.

Communication dated Oct. 19, 2005 from the U.S. Patent and Trademark Office in re U.S. Appl. No. 09/870,144, filed May 30, 2001, now U.S. Patent No. 7,328,059, by Sevick-Muraca et al.

Communication dated Jun. 14, 2006 from the U.S. Patent and Trademark Office in re U.S. Appl. No. 09/870,144, filed May 30, 2001, now U.S. Patent No. 7,328,059, by Sevick-Muraca et al.

Communication dated Feb. 14, 2007 from the U.S. Patent and Trademark Office in re U.S. Appl. No. 09/870,144, filed May 30, 2001, now U.S. Patent No. 7,328,059, by Sevick-Muraca et al.

Communication dated Jun. 29, 2007 from the U.S. Patent and Trademark Office in re U.S. Appl. No. 09/870,144, filed May 30, 2001, now U.S. Patent No. 7,328,059, by Sevick-Muraca et al.

* cited by examiner

METHOD AND SYSTEM FOR NEAR-INFRARED FLUORESCENCE CONTRAST-ENHANCED IMAGING WITH AREA ILLUMINATION AND AREA DETECTION

RELATED APPLICATIONS

This application claims the benefit under 35 U.S.C. § 119 (e) of U.S. Provisional Application Ser. No. 60/480,526 filed Jun. 20, 2003.

GOVERNMENT RIGHTS

This invention was made with Government support from the National Institute of Health, Contract No. R01 CA67176, and R01 EB002107. The government may have certain rights in this invention.

TECHNICAL FIELD OF THE INVENTION

The present invention relates generally to biomedical imaging and, more particularly, to a method and system for near infrared fluorescence contrast-enhanced imaging with area illumination and area detection.

BACKGROUND OF THE INVENTION

Fluorescent contrast agents have been developed and/or employed that enhance the optical detection of diseased tissues. These agents excite and re-emit at near-infrared (NIR) wavelengths, which deeply penetrate tissues. Localization of a contrast-enhanced target in three dimensions necessitates: (1) rapid and precise acquisition of fluorescence measurements; (2) accurate prediction of these measurements using an appropriate theoretical model of light propagation through tissues; and (3) tomographic reconstruction of model parameters, which include optical and fluorescent properties of tissues, using an optimization routine that minimizes the differences between the experimental and predicted fluorescence data. Steady-state and time-resolved experimental measurements of diffuse fluorescence have been used to localize a contrast-enhanced target. The steady-state measurements provide information regarding the spatial origin of fluorescent photons, and the time-resolved measurements provide additional information regarding fluorescence decay kinetics, which may render functional information about the environment in which the fluorophores reside.

Experimental measurements of diffuse fluorescence acquired using point illumination and point detection techniques have been incorporated into tomographic reconstruction algorithms. In order to adequately probe a tissue volume using these techniques, illumination and detection must occur via fiber optic at several points about the tissue volume. Disadvantages with point illumination and point detection include (1) possible failure to sufficiently excite the contrast-enhanced target and (2) the production of sparse data sets, which make the underdetermined inverse problem difficult to solve.

SUMMARY OF THE INVENTION

A method and system for near-infrared fluorescence contrast-enhanced imaging with area illumination and area detection are provided. In one embodiment, a method for biomedical imaging includes directing time-varying excitation light at a surface area of a light scattering material, the material comprising a fluorescent target. Time-varying emission light from the fluorescent target is detected, substantially at a two-dimensional sensor surface, in response to the time-varying excitation light stimulating the fluorescent target. The time-varying emission light is filtered to reject excitation light re-emitted from the material. A three-dimensional image of the fluorescent target is generated based on the detection substantially at the sensor surface.

Embodiments of the invention provide a number of technical advantages. Embodiments of the invention may include all, some, or none of these advantages. An approach employed herein involves area illumination and area detection on the same tissue-like surface. This approach overcomes the disadvantages associated with point illumination and point detection given that (1) fluorophores within a large tissue volume are more efficiently excited via area illumination and (2) significantly more data is provided via area detection. In addition, non-contact imaging is possible. Some applications may arise in medical imaging of diseased tissues and intraoperative 3D identification of diseased (and tumor) lesion margin for effective and complete resection of diseased tissue, among others.

Other advantages may be readily ascertainable by those skilled in the art from the following figures, description, and claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EXAMPLE EMBODIMENTS OF THE INVENTION

Figure 1:
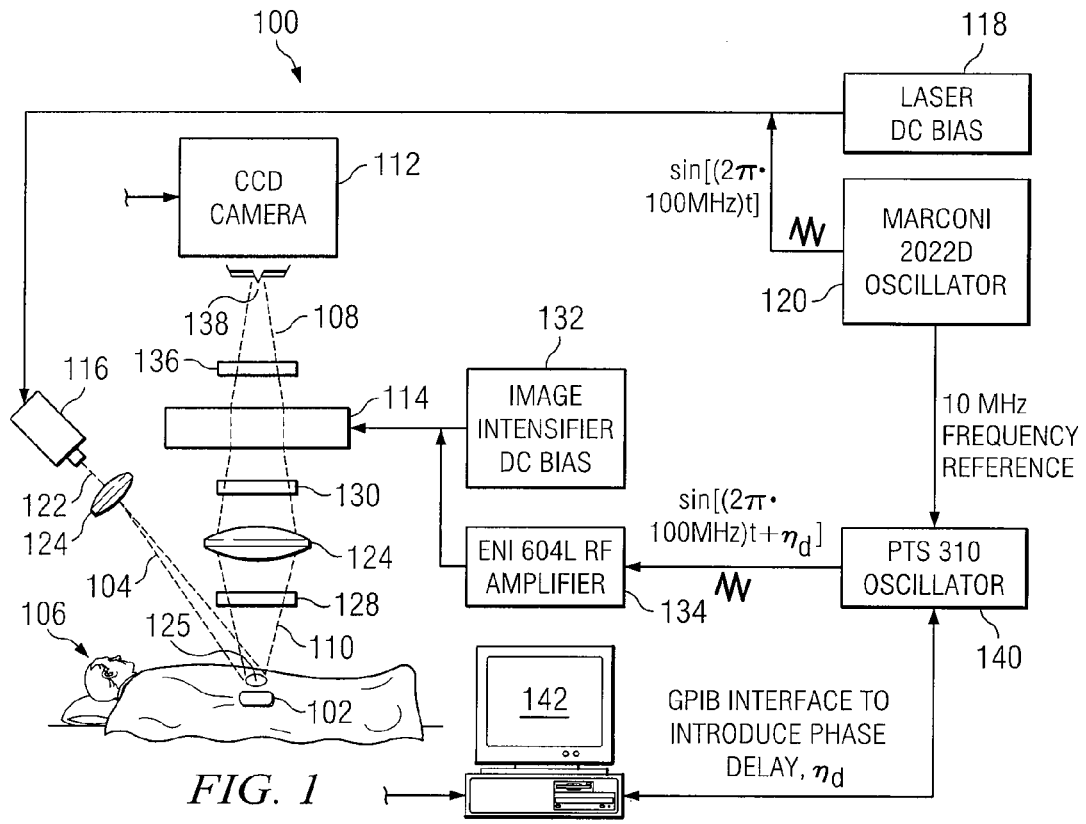
FIG. 1 is a schematic illustrating a system for near-infrared ("NIR") frequency-domain photon migration ("FDPM") measurements according to one embodiment of the present invention.

FIG. 1 is a schematic illustrating a system for excitation area illumination and area detection using near-infrared ("NIR") frequency-domain photon migration ("FDPM") imaging techniques according to one embodiment of the present invention. In particular, system 100 generates three-dimensional ("3D") images of fluorescent target 102 within a light scattering material (e.g., tissue) based on emission light detected at a two-dimensional ("2D") sensor surface. At a high level, system 100 delivers an intensity-modulated excitation light 104 into the tissue of a body 106 to cause stimulated emission of fluorescent target 102. Emission light 108 from the fluorescent target 102 is detected by intensified charge-coupled camera (ICCD) 112 via gain modulated image intensifier 114. A 3D image of fluorescent target 102 is generated based, at least in part, on excitation light 104 and emission light 108. System 100 provides several advantages over the prior art such as, for example, the ability to reconstruct a 3D image from data collected at a 2D surface with contact. The present invention contemplates more, less, or different components than those shown in system 100 of FIG. 1.

Referring to FIG. 1, system 100 includes a laser diode 116 coupled to a laser DC bias 118 and a reference frequency generator 120. As a result, laser diode 116 generates source light 122, intensity-modulated excitation light. In one embodiment, source light 122 comprises 785-nanometer ("nm") excitation light provided by a 70-milliWatt ("mW") laser diode 116. Additionally, a temperature controller (not illustrated) may be included in system 100 to assist in maintaining the optical power and the wavelength of laser diode 116; however, other suitable wavelengths and sources may be used. Source light 122 may comprise other suitable NIR light such as, for example, 700-nm to 900-nm light. Source light 122 passes through lens 124A to produce an expanded beam of excitation light 104 for illuminating a surface area 125 of body 106. Surface area 125, in one embodiment, is approximately 9 centimeters squared ($cm^2$) in size. Surface area 125 may comprise other suitable areas ranging from 1 $cm^2$ to 100 $cm^2$. Surface area 125 is illuminated with excitation light 104 for stimulating fluorescent target 102. Fluorescent target 102 comprises a fluorescent contrast agent (e.g., Indocyanine Green ("ICG")) that emits light in response to excitation light 104. In one embodiment, ICG is excited at 780 nm and emits at 830 nm, has an extinction coefficient of 130,000 $M^{-1}$ $cm^{-1}$, a fluorescent lifetime of 0.56 ns and a quantum efficiency of 0.016 for the 780/830 nm excitation/emission wavelengths. After illuminating surface area 125, light is re-emitted from body 106.

Re-emitted light 110 includes emission light 108 and reflected excitation light. To minimize the excitation light delivered to image intensifier 114, a band-pass filter 128 centered around the emission wavelength and a band-rejection filter 130 centered around the excitation wavelength are used in combination to substantially reject the excitation wavelength from re-emitted light 110 and to provide emission light 108. Emission light 108 substantially comprises light emitted by fluorescent target 102 as a result of excitation light 104 stimulating fluorescent target 102. Band-pass filter 128 and band-rejection filter 130 may be coupled via lens 124B (e.g., 50-mm lens). In one embodiment, band-pass filter 128 and band-rejection filter 130 comprise an 830-nm image quality bandpass interference filter and a 785-nm holographic band-rejection filter, respectively. Alternatively, system 100 may use any suitable combination of filters such as, for example band-pass filters, long-pass filters, holographic notch filters, band-rejection filters or any combination thereof, or any optical scheme to reject the excitation wavelength enabling registration of the emission wavelength. After the combined filters substantially remove the excitation wavelength, emission light 108 is amplified by image intensifier 114.

In one embodiment, image intensifier 114 includes a photocathode face that converts photons to electrons, a multichannel plate ("MCP") that multiplies the electronic signal by avalanche multiplication, and a phosphorescent screen that converts electrons into an optical image. In one embodiment, image intensifier 114 is a fast intensifier of the variety manufactured by Litton Electronics, Inc., which enables modulation by applying a DC bias via image intensifier bias 132 and an RF signal via an RF amplifier 134 between the photocathode and the MCP; however, other suitable image intensifiers may be utilized. In the illustrated embodiment, the intensifier gain of image intensifier 114 and the intensity of excitation light 104 are sinusoidally modulated at 100 MHz by oscillators 120 and 140, both of which are phase-locked by a 10 MHz reference signal. By modulating laser diode 116 and image intensifier 114 at the same frequency, homodyning results in a steady-state image on the phosphorescent screen. The image from the phosphorescent screen is focused through a lens 136 (e.g., 105-mm lens) onto a two-dimensional sensor surface 138 of camera 112, in order to provide area detection. As used herein, the term "two-dimensional sensor surface" means a substantially two-dimensional surface determined by the sensors of camera 112. Sensor surface 138 may be flat, curved, bent, or arranged in any suitable surface. In one embodiment, sensor surface 138 comprises a 16 $cm^2$ flat surface. Camera 112, in the illustrated embodiment, has a 512×512 array of CCD detectors configured to provide a corresponding pixelated image.

In operation, following each acquired image, a phase delay between image intensifier 114 and laser diode 116 is induced by stepping the phase of image intensifier 114 between 0° and 360° relative to the phase of laser diode 116 modulation. Preferably, control between oscillator 140 and the processor is obtained by a conventional general purpose interface bus ("GPIB") 142; however, other suitable interfaces may be utilized. Images from the phosphorescent screen image intensifier 114 may then be gathered at each phase delay by camera 112 to determine phase-sensitive fluorescence intensity. In one embodiment, each image, may contain 128×128 pixels of intensity counts and be acquired by use of a 0.4-s CCD exposure time. A fast Fourier transform of the phase-sensitive fluorescence intensities acquired at each CCD pixel may be performed to compute the amplitude and phase-shift of emission light 108 at each CCD pixel. Prior to generating a 3D image of fluorescent target 102 based on the amplitude and phase-shift of emission light 108, the predicted amplitude and phase-shift of emission light 108 may be determined by the coupled frequency-domain diffusion equations (1) and (2) discussed below; however, the amplitude and phase may be determined by any other suitable mathematical model of light propagation. However, the solution to these coupled equations requires the spatial distribution of amplitude and phase-shift of incident excitation light 104. Since it is difficult to create a beam of intensity-modulated excitation light that is spatially uniform in both amplitude and phase-shift, the spatial distribution of excitation light 104 may be experimentally determined.

Figure 2:
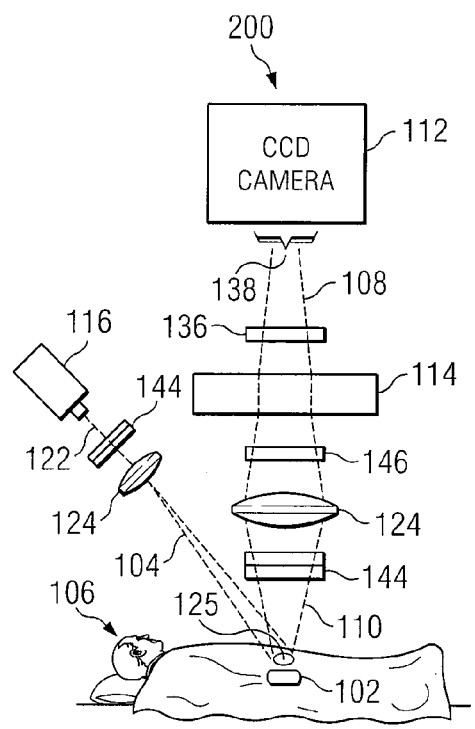
FIG. 2 is a schematic illustrating a system for detecting re-emitted excitation light in accordance with one embodiment of the present invention.

In one embodiment, system 100 may be altered to experimentally determine the amplitude and phase-shift of incident excitation light 104 in the following manner: (1) linear polarizers 144 are positioned at the output of laser diode 116 and the input of CCD camera 112; (2) aperture of lens 124 may be minimized; and (3) bandpass filter 128 and band-rejection filter 130 are replaced with a neutral density filter 146 to provide system 200 illustrated in FIG. 2. Generally, re-emitted light 110 includes both specularly-(or singly-) reflected excitation light and multiply-reflected excitation light. Since singly-reflected excitation light may be representative of incident excitation light 104, re-emitted light 110 is compared to multiply-reflected excitation light to determine the spatial distribution of the singly-reflected excitation light and thus the spatial distribution of incident excitation light 104.

In one aspect of operation, the polarization angle of linear polarizers 144 are first oriented parallel to one another to predominately detect specularly-reflected excitation light. Images of phase-sensitive excitation light intensity of this detected light may be determined using the procedure described above with regard to FIG. 1, predominantly resulting in images representative of specularly-reflected excitation light. In order to substantially remove multiply-scattered excitation light intensities from these images, the polarization angles of linear polarizers 144 may be adjusted to determine images of phase-sensitive excitation light intensity for multiply-reflected light. In general, linearly polarized light incident on a tissue surface and multiply-reflected by fluorescent target 102 reemerges from the tissue depolarized with an equal probability of having a polarization angle parallel or perpendicular to incident polarization angle. Therefore, to substantially remove image intensities representative of multiply-reflected excitation light from the images of phase-sensitive excitation light intensity, a second set of images of phase-sensitive excitation light intensity representative of multiply-reflected excitation light may be acquired after orienting the polarization angles of polarizer 144 perpendicular to one another. The second set of images may be subtracted from the first set of images to provide phase-sensitive excitation light intensity of the specularly-reflected excitation light. Afterward, a fast Fourier transform of the phase-sensitive images representative of the specularly-reflected excitation light may be performed to determine the spatial distribution of the amplitude and phase of incident excitation light 104. Once the spatial distribution of both incident excitation light 104 and emission light 108 are determined, the mathematical expression discussed in relation to FIG. 4 may be used to iteratively converge upon the optical properties of fluorescent target 102.

Figure 3:
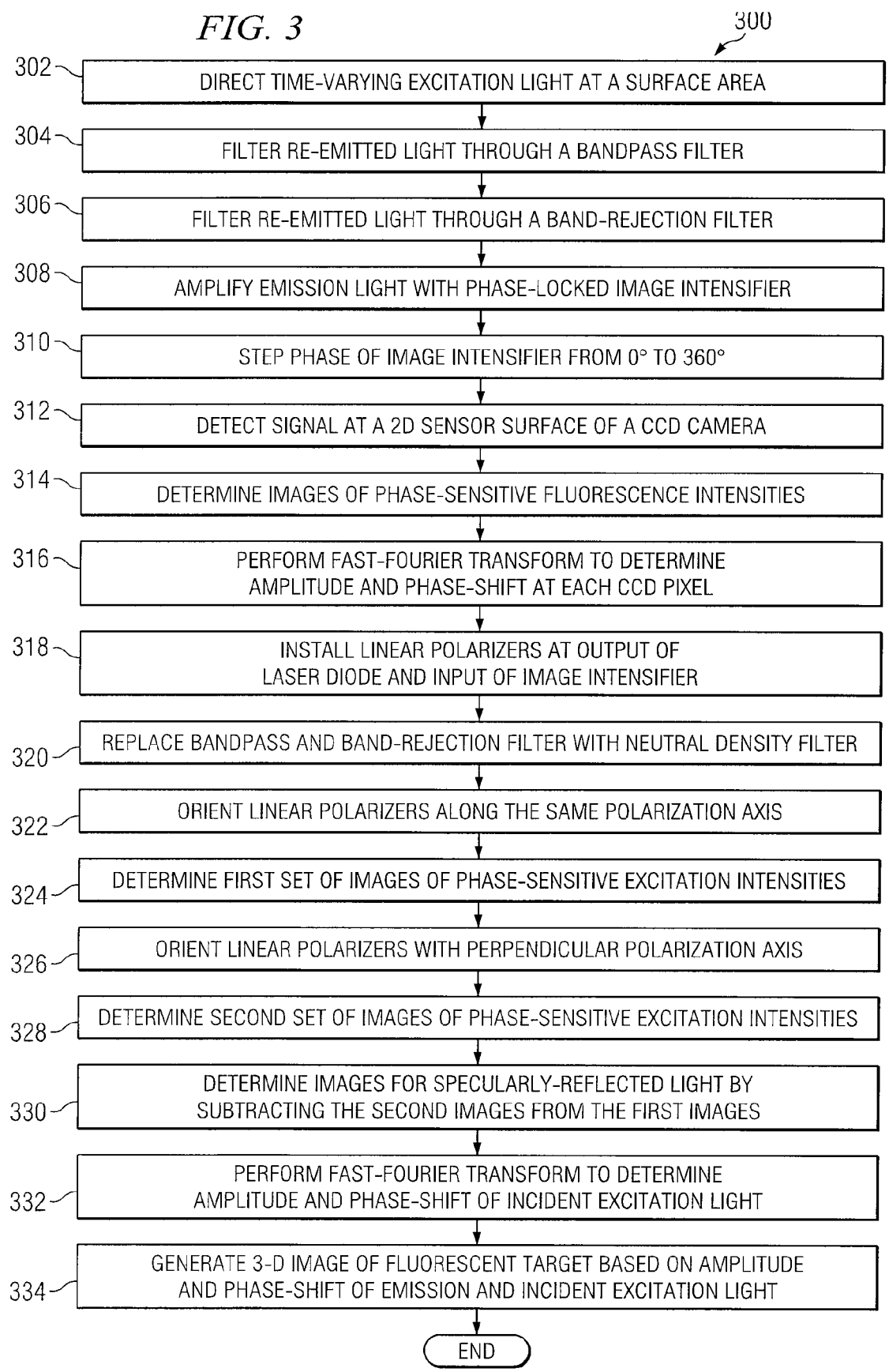
FIG. 3 is a flow chart illustrating a method for tomographic fluorescent imaging in accordance with one embodiment of the present invention.

FIG. 3 is an example flow diagram illustrating a method 300 for generating a 3D image from light detected on a two-dimensional sensor surface. Method 300 is described with respect to system 100 and 200 of FIGS. 1 and 2, respectively, but method 300 could also be used by any other system. Moreover, system 100 and 200 may use any other suitable techniques for performing these tasks. Thus, many of the steps in this flow chart may take place simultaneously and/or in different orders as shown. Moreover, system 100 and 200 may use methods with additional steps, fewer steps, and/or different steps, so long as the methods remain appropriate.

At a high level, method 300 illustrates two processes for generating a 3D image: an emission-light determination process and an incident-light determination process. The emission-light determination process is illustrated in steps 302 to 316, and the incident-light determination step is illustrated in steps 318 to 332. Method 300 begins at step 302 where a time-varying excitation light 104 is directed at a surface area 125 of body 106 to stimulate fluorescent target 102. Next, at step 304, re-emitted light 110 from body 106 is filtered by band-pass filter 128 to pass a subband of re-emitted light 110 including the emission wavelength to band-rejection filter 130 while substantially rejecting other wavelengths. Band-rejection filter 130 rejects a subband of the received light, including the excitation wavelength, and passes emission light 108 to image intensifier 114 at step 306. At step 308, image intensifier 114 is phase-locked to laser diode 116 and amplifies emission light 108. In order to determine phase-shift data for emission light 108, image intensifier 114 is stepped between 0° and 360° relative to the phase of laser diode modulation at step 310. Next, at step 312, the amplified emission light 108 is detected at a two-dimensional surface area 138 of CCD camera 112 to electronically recover intensity data of emission light 108. Images of phase-sensitive fluorescence intensities are determined for each CCD pixel at step 314. At step 316, a fast Fourier transform of the phase-sensitive fluorescence intensities is performed to compute spatial distribution of the fluorescence intensity and phase-shift for each CCD pixel. In short, system 100 has now experimentally determined the spatial distribution of emission light 108 and is ready to determine the spatial distribution of incident excitation light 104.

Figure 4:
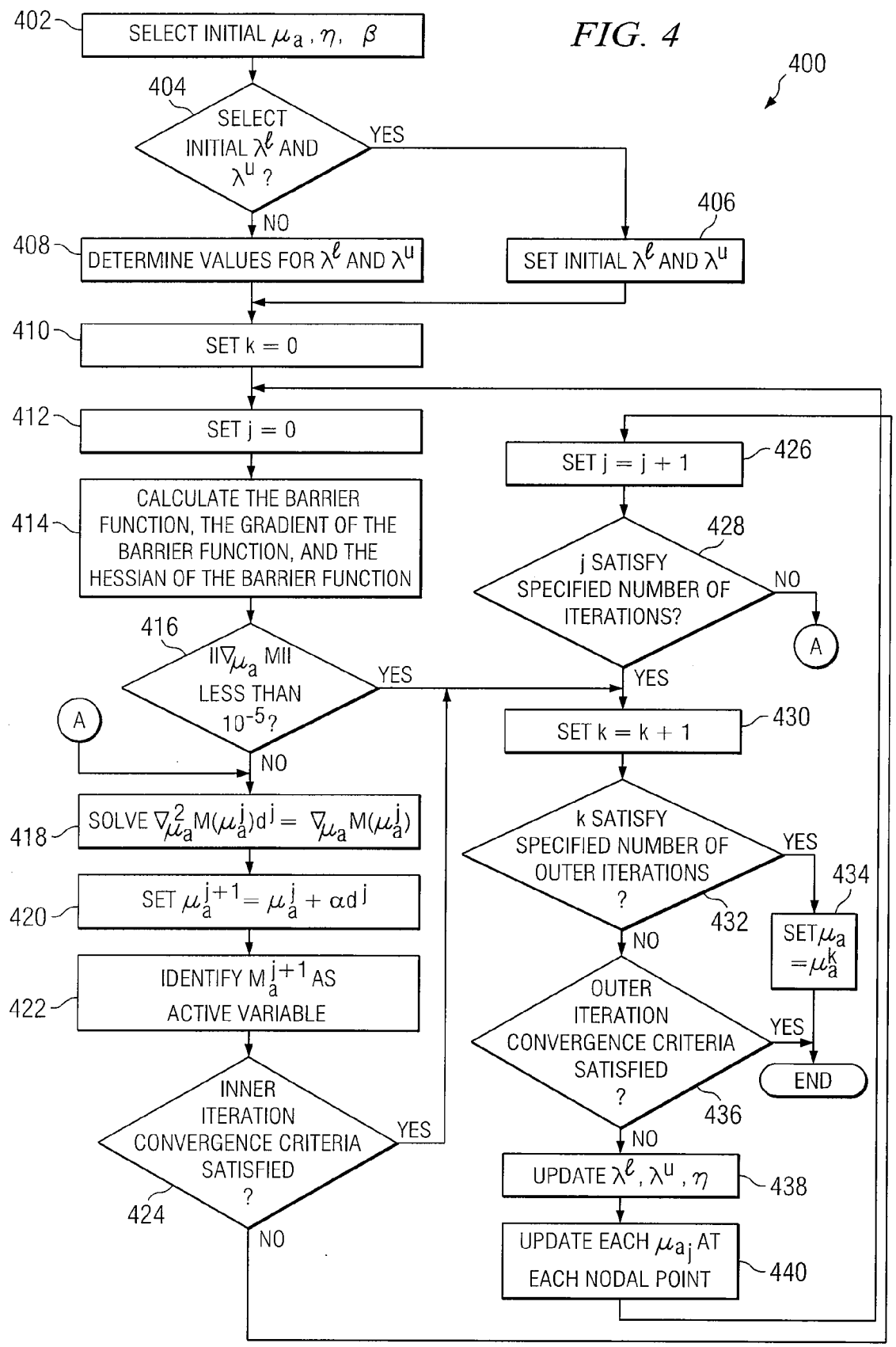
FIG. 4 illustrates one embodiment of generation step of FIG. 3.

The excitation-light determination step begins at step 318 where linear polarizers 144 are installed at the output of laser diode 116 and the input of image intensifier 114. Next, at step 320, bandpass rejection filter 128 and band-rejection filter 130 are replaced with neutral density filter 146. In order to determine the spatial distribution for excitation light, the polarization axis of linear polarizers 144 are aligned along the same axis at step 322. A first set of images of phase-sensitive excitation intensities is determined at step 324, which predominantly represents specularly-reflected excitation light. At step 326, linear polarizers 144 are aligned with their polarization axis substantially perpendicular to detect multiply-scattered excitation light. A second set of images of phase-sensitive excitation intensities is determined at step 328, which predominantly represents multiply-reflected excitation light. In order to substantially remove multiply-reflected excitation intensities from the first set of images, the second set of images is subtracted from the first set of images to determine images of phase-sensitive excitation intensities for specularly-reflected excitation light at step 330. Since specularly-reflected excitation light is representative of incident excitation light 104, a fast Fourier transform of the images of phase-sensitive excitation intensities for specularly-reflected excitation light computes the spatial distribution of excitation intensity and phase-shift for incident excitation light 104 at step 332. Finally, at step 334, a 3D image of fluorescent target 102 is generated based on the spatial distribution of intensity and phase-shift for incident excitation light 104 and emission light 108. FIG. 4 illustrates one embodiment of determining the 3D image corresponding to step 334 above, in accordance with the penalty/modified barrier function (PMBF) method.

FIG. 4 illustrates one embodiment of step 334 of FIG. 3 for generating a 3D image of fluorescence absorption coefficients. Method 400 is described with respect to system 100 and 200 of FIGS. 1 and 2, respectively, but method 400 could also be used by any other system. Moreover, system 100 and 200 may use any other suitable techniques for performing these tasks. Thus, many of the steps in this flow chart may take place simultaneously and/or in different orders as shown. Moreover, system 100 and 200 may use methods with additional steps, fewer steps, and/or different steps to generate a 3D image of fluorescence absorption coefficients.

To aid in understanding the various mathematical aspects of method 400, the following tables of selected variables is listed:

| | |
|---|---|
| $\vec{r}$ | position |
| c | speed of light |
| S | source |
| n | number of nodal points |
| ω | angular modulation frequency |
| $\mu_{a_{xi}}$ | absorption coefficient due to chromophore |
| $\mu_{a_{xf}}$ | absorption coefficient due to fluorophore |
| $\mu_a$ | total absorption at the emission wavelength is equal to the absorption owing to nonfluorescent chromophores $\mu_{a_{xi}}$ and fluorescent choromophore, $\mu_{a_{mf}}$ |
| D | optical diffusion coefficient = $\frac{1}{3}[\mu_{a_{x,m}} + \mu'_{s_{x,m}}]$ |
| $\mu'_{s_{x,m}}$ | isotropic scattering coefficient |
| $\mu_{a_{x,m}}$ | total absorption coefficient |
| Φ | complex fluence |
| φ | quantum efficiency |
| τ | fluorescence lifetime |
| Ω | volume |
| $I_{AC}$ | intensity amplitude |

-continued

| Symbol | Description |
|---|---|
| θ | phase-shift |
| K | global stiffness matrices |
| b | global vector in FEM stiffness equation containing source terms |
| E | error function |
| $N_D$ | number of detectors |
| $N_S$ | number of source |
| g | gradient vector ∇E |
| d | Newton direction |
| α | step length |
| H | Hessian matrix $\nabla^2 E$ |
| l | lower bound of the absorption coefficient owing to fluorophore |
| u | upper bound of the absorption coefficient owing to fluorophore |
| $L^1$ | Natural coordinate |
| $B(\mu_a)$ | active set (lower bound) |
| $B'(\mu_a)$ | active set (upper bound) |
| $C(\mu_a)$ | free variable set |
| ε | tolerance of lower and upper bound |
| λ | Lagrange multipliers |
| $\lambda^l$ | Lagrange multiplies for lower bound |
| $\lambda^u$ | Lagrange multipliers for upper bound |
| M | modified barrier penalty function |
| $h_i(\mu_a)$ | bound constrain |
| $f(h_i(\mu_a))$ | quadratic penalty/barrier term of PMBF |
| $\phi(h_i(\mu_a))$ | quadratic extrapolation method |
| $S_i$ | shifting parameter |
| η | barrier parameter |
| β | parameter defines how close the extrapolation will get to singularities of logarithm term |
| $q_i^1, q_i^2, q_i^3$ | coefficient of the quadratic function |
| γ | reduction factor of the barrier parameter |
| k | outer iteration number |
| j | inner iteration number |
| $\gamma_1^k, \gamma_2^k, d_1$ and $d_2$ | convergence criteria |
| $\epsilon_1$ | reconstruction error |

Generally, method 400 uses the modified barrier penalty function to reconstruct a 3D image of fluorescence absorption coefficients. However, prior to discussing method 400; additional information will be provided.

Diffusely propagated fluorescence is predicted by the coupled diffusion equations (1) and (2) given the optical properties of the tissue. The numerical solution of the diffusion equation may be needed to provide sufficiently accurate estimates of the fluence on the boundary of the tissue for the image reconstruction (or inverse) problem. The coupled diffusion equation used in optical tomography at a given modulation frequency $f(\omega=2\pi f \text{ rad})$ is given by:

$$-\nabla \cdot [D_x(\vec{r})\nabla \Phi_x(\vec{r},\omega)] + \left[\frac{i\omega}{c} + \mu_{a_{xi}}(\vec{r}) + \mu_{a_{xf}}(\vec{r})\right]\Phi_x(\vec{r},\omega) = S \text{ on } \Omega \quad (1)$$

$$-\nabla \cdot [D_m(\vec{r})\nabla \Phi_m(\vec{r},\omega)] + \left[\frac{i\omega}{c} + \mu_{a_m}(\vec{r})\right]\Phi_m(\vec{r},\omega) = \phi\mu_{a_{xf}}\frac{1}{1-i\omega\tau}\Phi_x(\vec{r},\omega) \text{ on } \Omega \quad (2)$$

Here, $\Phi_D$ and $\Phi_m$ are the AC components of the excitation and emission photon fluence (photons/cm²/sec) at position r, respectively; ω is the angular modulation frequency (rad/s); c is the speed of light within the medium (cm/s); $\mu_{a_{xi}}$ is the absorption due to chromophores (cm⁻¹); and $\mu_{a_{xf}}$ is the absorption due to fluorophores (cm⁻¹). $D_{x,m}$ is the optical diffusion coefficient equivalent to $\frac{1}{3}(\mu_{a_{x,m}}+\mu_{s_{x,m}}')$, where $\mu_{s_{x,m}}'$ is the isotropic scattering coefficient (cm⁻¹) and $\mu_{a_{x,m}}$ is the total absorption coefficient, at the respective wavelengths. The total absorption at the emission wavelength, $\mu_{a_m}$, is equal to the absorption owing to nonfluorescent chromophores, $\mu_{a_{xi}}$ and fluorescent chromophores, $\mu_{a_{xf}}$. The right hand term of equation (2) describes the generation of fluorescence within the medium. The term φ represents the quantum efficiency of the fluorescence process, which is defined as the probability that an excited fluorophore will decay radiatively, and τ is the fluorophore lifetime (ns). Note that the source term couples with the solution of excitation fluence described by equation (1). The numerical solutions for the excitation and emission fluence distributions given in equations (1) and (2), respectively, may be obtained using the Robin boundary condition. Other suitable mathematical models of light propagation and emission generation may be used to obtain the excitation and/or emission fluence distributions.

The source term S in equation (1) depends on the measurement types. For point illumination, the excitation source is represented as $$S = \sum_{i=1}^{n_1} S\delta(\vec{r}-\vec{r}_s) \quad (3)$$

where $r_s$ is the positional vector of the illuminating point on the surface of the phantom; δ is the Dirac delta function representing the source of excitation at a single point; $n_1$ is the total number of simultaneous points of illumination, which is typically one. For area illumination, the area of the planar source can be discretized into a number of triangular finite elements and the source within a surface element in area coordinate is represented by $$S = \sum_i^3 L_i^1 S_i \quad (4)$$

where the $L_i^1$ are the natural co-ordinates for the triangle and $S_i$ is the source value at each node (i). The source term corresponding to the area illumination can be approximated as the summation of simultaneous and closely positioned multiple point sources as given by equation (4).

The Galerkin finite element method with tetrahedral in three-dimensions may be used to solve the differential equations (1) and (2). Local stiffness matrices may be formed for each element and then these matrices may be combined into two global stiffness matrices, $K_x$ for the excitation equation and $K_m$ for the emission equation. The solutions of the differential equations are obtained by solving the complex equations:

$$K_{x,m}\Phi_{x,m}=b_{x,m} \quad (5)$$

where $b_{x,m}$ is the right hand side of excitation and emission equations. The discretization process converts the continuous problem into a problem with finite number of unknowns by expressing the unknown field variables, which are the absorption coefficients owing to fluorophore $\mu_{a_{xf}}$ in terms linear interpolation functions within each element. The linear functions are defined in terms of the values of the field variables at each node of the element. Therefore, the nodal values of the field variables become the unknowns to the image problem.

From the solution of $\Phi_{x,m}$ the values of the amplitude, $I_{AC_{x,m}}$, and phase shift, $\theta_{x,m}$, can be determined from the relationship:

$$\Phi_{x,m}=I_{AC_{x,m}}\exp(-i\theta_{x,m}) \quad (6)$$

Two finite element meshes may be employed when solving the modified barrier penalty function. The first may contain 33431 nodes with 163285 tetrahedral elements (denoted below as Mesh 1) while the second, more refined mesh may contain 38919 nodes with 193137 tetrahedral elements (defined as Mesh 2). 1205 seconds and 1738 seconds of CPU time may be required to solve the coupled excitation and emission equations for Mesh 1 and Mesh 2, respectively. All the computations in this paper may be performed on a SUN-blade 100 UNIX workstation.

Information regarding the error function will also be provided prior to discussing method 400. The error function considered for the image reconstruction problems is as follows (for brevity we will use $\mu_a$ for $\mu_{a_{xf}}$ henceforth):

$$E(\mu_a, \omega) = \frac{1}{2} \sum_{p=1}^{N_D} \left[ (\log(Z_p)_c - \log(Z_p)_m)_j (\log(Z_p)_c^* - \log(Z_p)_m^*) \right] \quad (7)$$

where E is the error function associated with measurements, $Z_p$ is comprised of referenced fluorescent amplitude, $$I_{AC_{ref_p}},$$

and referenced phase shift $\theta_{ref_p}$ measured at boundary point, p, in response to planewave illumination. Specifically the referenced measurement at boundary point p is given by:

$$Z_p = I_{AC_{ref_p}} \exp(i\theta_{ref_p}) \quad (8)$$

The experimental values of fluorescence modulated amplitude $I_{AC_p}$, may be divided by the maximum fluorescence experimental value from the collected reflectance data set, $I_{AC_{max}}$ in order to compute the referenced amplitude values, $$I_{AC_{ref_p}}$$

The experimental fluorescence phase shift, at the position where the maximum fluorescence $I_{AC_{max}}$ was obtained, may be determined as $$\theta_{at\, I_{AC_{max}}}$$

and subtracted from all experimental fluorescence phase shift values, $\theta_p$ in the collected reflectance data sets to obtained referenced phase shift values, $\theta_{ref_p}$. These represent the "referenced" measurements:

$$I_{AC_{ref_p}} = \frac{I_{AC_p}}{I_{AC_{max}}}; \theta_{ref_p} = \theta_p - \theta_{at\, I_{AC_{max}}} \quad (9)$$

The predicted fluorescence $$I_{AC_{ref_p}} \text{ and } \theta_{ref_p}$$

may be computed by solving the coupled diffusion equations (1 and 2) using the finite element method and may be similarly normalized to obtain the calculated values. Other suitable methods may be used to calculate these values. The referenced data are normalized in this manner in order to reduce, minimize, or eliminate instrument functions.

The error in equation (7) is reported for values of tissue absorption owing to fluorescent contrast agent. The subscript c denotes the values calculated by the forward solution and the subscript m denotes the experimental value. $N_D$ denotes the number of detectors on the surface. The superscript * denotes the complex conjugate of the complex function of the referenced measurements.

The discussion regarding the coupled diffusion equations (1) and (2) and the error function (7) provides a basis for the modified barrier penalty function, M (termed hereafter as the barrier function), which is stated as follows:

$$\min_{\mu_a} M(\mu_a, \lambda, \eta) = E(\mu_a) - \eta \sum_{i=1}^{n} \lambda_i^l f(\mu_{a_i} - l) + \lambda_i^u f(u - \mu_{a_i}) \quad (11)$$

where $\eta$ is a penalty/barrier term; n is the number of nodal points; and $\lambda^l$ and $\lambda^u$ are vectors of Lagrange multipliers for the bound constraints for the lower and the upper bounds, respectively. From equation (11); one can see that the simple bounds are included in the barrier function M.

Function $f$ may be defined as:

$$f(h_i(\mu_a)) = \quad (12)$$

$$\begin{cases} \log\left(s_i + \frac{h_i(\mu_a)}{\eta}\right) & \text{for } i = 1, 2, \ldots, n \text{ if } h_i(\mu_a) \geq -\beta s_i \eta \\ \varphi(h_i(\mu_a)) & \text{for } i = 1, 2, \ldots, n \text{ if } h_i(\mu_a) < -\beta s_i \eta \end{cases}$$

where $$\varphi(h_i(\mu_a)) = \frac{1}{2} q_i^2 (h_i(\mu_a))^2 + q_i^2 (h_i(\mu_a)) + q_i^3 \quad (13)$$

$h_i(\mu_a)$ represents all the bound constraints $\{(\mu_{a_i}-l)$ and $(u-\mu_{a_i})\}$; and $s_i$ is positive-valued shifts used in the enlargement of the feasibility region for the lower and the upper bounds, respectively. In one embodiment, the $s_i$ is set to 1.0 for all computations. The coefficients $q_i^1$, $q_i^2$ and $q_i^3$ of the quadratic function in equation (13) are chosen so that their values, and their first and second derivatives match those of the logarithmic term in equation (12) at the point $h_i(\mu_a) = -\beta s_i \eta$. The coefficients of the quadratic function are given as:

$$q_i^1 = \frac{-1}{(s_i \eta (1 - \beta))^2} \quad (14)$$

$$q_i^2 = \frac{1 - 2\beta}{s_i \eta (1 - \beta)^2} \quad (15)$$

-continued $$q_i^3 = \frac{\beta(2-3\beta)}{(2(1-\beta)^2)} + \ln(s_i(1-\beta)) \qquad (16)$$

The coefficients are dependent on both $\beta$ and $\eta$, and thus have to be updated for any changes of $\beta$ and $\eta$. The values of $\beta$ define how close to the singularities the logarithmic terms described in equation (12) are extrapolated. Consequently we define a very simple differentiable modified barrier penalty function by equation (11) that is used to assess the quality of the solution. This function has an extremely simple structure so that the overhead for using the barrier function instead of the original error function given by equation (7) is negligible for function evaluation or for computing gradients and Hessian as discussed below.

The PMBF method 400 is performed in two stages, an inner and an outer stage illustrated in FIG. 4. The outer iteration updates the Lagrange multiplier $\lambda$, parameter $\beta$, and the barrier parameter $\eta$. Formulations used to update these parameters at each outer iteration are provided in the discussion below. Using the calculated values of the parameter $\lambda$, an unconstrained technique may be applied to minimize the penalty barrier function described by equation (11). Once satisfactory convergence within the inner iteration is reached, the variables in the outer iteration are recalculated to check for satisfactory convergence in the outer iteration. If unsatisfactory, the Lagrange multipliers and the barrier parameters are updated and another unconstrained optimization is started within the inner iteration.

Method 400 begins at step 402 where initial values of $\mu_a$, $\eta$ and $\beta$ are selected. The initial value for $\mu_a$, the absorption coefficient due to fluorophore, is a positive value typically selected from the range of 0 to 0.1 cm$^{-1}$. The initial value for $\eta$, the barrier parameter, is an arbitrary positive value and is typically $10^{-1}$ or $10^{-2}$. The initial value for $\beta$ is a parameter that defines how close to the singularities the logarithmic terms in the modified barrier penalty function are extrapolated. The values of $\beta$ are typically not too small (e.g., $0 \leq \beta \leq 0.5$) or very close to one (i.e., $\beta=0.99$). For example, the value of $\beta$ may be set to 0.9. Next, at decisional step 404, if the initial values of $\lambda^l$, an initial Lagrange multiplier for a lower bound, and $\lambda^u$, an initial Lagrange multiplier for an upper bound, are selected, then, at step 406, the values are set to equal values such as, for example, 1, 10, 100 and 1000. If the initial values of $\lambda^l$ and $\lambda^u$ are not initially selected, then, at step 408, the values of $\lambda^l$ and $\lambda^u$ are determined. In one embodiment, the initial values of $\lambda^l$ and $\lambda^u$ are determined using a vector $\lambda^0$ that minimizes the least-squares unconstrained problem:

$$\min_{\lambda \geq 0} \| \nabla_{\mu_a} E(\mu_a^0) - \lambda \nabla_{\mu_a} f(h(\mu_a^0)) \|_2^2 \qquad (17)$$

this gives the formula:

$$\lambda(\mu_a^0) = A(\mu_a^0) \nabla_{\mu_a} E(\mu_a^0) \nabla_{\mu_a} f(h(\mu_a^0)) \qquad (18)$$

where $$A(\mu_a^0) = (\nabla_{\mu_a} f^T(h(\mu_a^0)) \nabla_{\mu_a} f(h(\mu_a^0))^{-1} \qquad (19)$$

The formulation of equation (18) requires calculation of all constraint gradients and the gradients of the error function $E(\mu_a^0)$ and inversion of the matrix $A(\mu_a^0)$. The inversion of this large (n×n) matrix in the reconstruction problem can be very costly. To reduce the computational cost, only the diagonal terms of the equation (18) may be used. Hence there is no need to invert the matrix. Using this least-square procedure the initial Lagrange multipliers for image reconstruction problem may be computed. After the initial values of $\mu_a$, $\eta$, $\beta$, $\lambda^l$ and $\lambda^u$ are set, the indices k, which identifies the current step of the outer stage, is set to zero at step 410.

Method 400 now executes the inner stage of the PMBF method by setting the indices j, which represents the current iteration of the inner stage, to zero at step 412. Next, at step 414, the barrier function, the gradient of the barrier function and the Hessian of the barrier function are calculated. The barrier function may be calculated by equation (11). During this calculation, an unconstrained optimization method may be used to optimize the unconstrained barrier function of equation (11) for each set of parameters $\lambda^k$ and $\eta^k$. The truncated Newton method with trust region (TN) may be used for the unconstrained optimization problem. The gradient based truncated Newton method is efficient and suitable for large-scale problem. The gradient of the barrier function may given by $$\nabla_{\mu_a} M(\mu_a, \lambda^k, \eta^k) = \qquad (20)$$

$$\begin{cases} \nabla_{\mu_a} E(\mu_a) - \eta^k \sum_{i=1}^{n} \frac{\lambda^k}{\left(\frac{h_i(\mu_a)}{\eta^k} + s_i\right)} \nabla h_{ix}(\mu_a) & \text{if } h_i(\mu_a) \geq -\beta^k s_i \eta^k \\ \nabla_{\mu_a} E(\mu_a) - \eta^k \sum_{i=1}^{n} \lambda^k \{q_i^1(h_i(\mu_a)) + q_i^2\} & \text{if } h_i(\mu_a) < -\beta^k s_i \eta^k \end{cases}$$

The gradients of the error function $\nabla_{\mu_a} E$ may be calculated by the analytical method using reverse differentiation technique. The Hessian of the barrier function may be determined as follows:

$$\nabla_{\mu_a}^2 M(\mu_a, \lambda^k, \eta^k) = \qquad (21)$$

$$\begin{cases} \nabla_{\mu_a}^2 E(\mu_a) - \eta^k \sum_{i=1}^{n} \frac{\lambda^k}{(h_i(\mu_a) + s_i \eta^k)^2} & h_i(\mu_a) \geq -\beta^k s_i \eta^k \\ \nabla_{\mu_a}^2 E(\mu_a) - \eta^k \sum_{i=1}^{n} \lambda^k \{q_i^1\} & h_1(\mu_a) < -\beta^k s_i \eta^k \end{cases}$$

$\nabla_{\mu_a}^2 E(\mu_a) \cdot d$ maybe calculated by the finite difference scheme, $$H(\mu_a) \cdot d = \frac{1}{\delta} \{[g(\mu_a + \delta d)] - g(\mu_a)\} \qquad (22)$$

where $\nabla_{\mu_a} E(\mu_a) = g(\mu_a)$ is the gradient; $\nabla_{\mu_a}^2 E(\mu_a) = H(\mu_a)$ is the Hessian of the error function $E(\mu_a)$; d is the Newton direction; and $\delta$ is (approximately) the square root of the machine precision. It may not be safe to perform finite differencing directly to $\nabla_{\mu_a}^2 M$ because of the singularity of the logarithmic function. The final summation in the formulation for $\nabla_{\mu_a}^2 M$ may be computed straightforwardly from the formulas above.

If the absolute value of the gradient of the barrier function is less than $10^{-5}$ at decisional step 416, then the inner stage ends and execution proceeds to step 430 of the outer stage. Otherwise, $\nabla_{\mu_a}^2 M(\mu_a^j) d^j = \nabla_{\mu_a} M(\mu_a^j)$ is solved at step 418 to determine the Newton direction d. The Newton direction d is computed as an approximation solution of the Newton equations:

$$(\nabla^2 M)d = -\nabla M \quad (23)$$

where $\nabla^2 M \equiv \nabla^2 M(\mu_a)$ is the Hessian matrix of second derivatives at the current solution designated by a vector $\mu_a$. The approximate solution of equation (23) may be obtained by the linear conjugate-gradient method, but the solution may alternatively be determined by any suitable method. This iterative method is "truncated" before the exact solution is obtained. The conjugate-gradient method (CG) corresponds to minimizing the quadratic model $$\min_d Q(d) = \frac{1}{2} d^T \nabla^2 M d + d^T \nabla M \quad (24)$$

$$s.t. \quad l - \mu_a \leq d \leq u - \mu_a \quad (25)$$

as a function of d over a sequence of subspaces of increasing dimension. Criteria must be determined and applied to find out whether convergence has been achieved. This method has two levels of iterations, with the 'outer-level' iteration determining the step length, and the 'inner-level' iteration computing the Newton direction using conjugate gradient method. A further issue for unconstrained minimization is what to do when the current Hessian $\nabla^2 M$ is not positive definite. Several approaches are used, among the most popular of which are so-called modified Newton method in which $d_j$ satisfies the linear system, $$(\nabla^2 M(\mu_a^j) + R)d^j = -\nabla M \quad (26)$$

where R is a positive semidefinite matrix. Different techniques have been used to calculate R so that $(\nabla^2 M(x^k) + R)$ is positive definite. An alternative globalization strategy in unconstrained optimization embodied in trust region methods, is to choose the step $d^j$ to minimize the local Taylor-series model subject to a limitation on the size of $\|d\|$, where various norms may appear in the trust-region constraints. To alleviate this difficulty, the conjugate gradient method with trust region may be used for unconstrained optimization problems. The procedure is described in the following paragraph as followed:

CG methods generate sequences $p^i$, $y^i$ where $p^i$ approximates iteratively the Newton direction $d^j$ and the conjugate direction $y^i$. The update scheme is $$p^{i+1} = p^i + \Lambda^i y^i \quad (27)$$

$$y^{i+1} = r^{i+1} + \rho p^i y^i \quad (28)$$

where $\Lambda^i$ minimizes the quadratic function Q(d) along the direction $y^i$ and $\rho^i$ is chosen so as to maintain conjugacy between the directions $y^i$. The CG terminates when the residual $r^i = -\nabla Q(p^i)$ is in norm below a prescribed tolerance or when a negative curvature direction $\tau_1 = (s^i)^T \nabla^2 M s^i \leq 0$ is encountered. This algorithm does not stop, but computes $\tau_1 > 0$ so that $\|p^i + \tau_1 y^i\| = \Delta$, where $\Delta$ is the trust region. Then update rule is $d^{i+1} = d^i + \tau_1 y^i$. The algorithm stops if the residual $\|r^i\|$ is below a given tolerance, or if $(y^i)^T \nabla^2 M y^i = 0$.

Next, at step 420, a new estimate of the absorption owing to fluorophore is determined by $\mu_a^{j+1} = \mu_a^j + \alpha d^j$, where $\alpha$ is the step length. The step length may be determined by an Armijo line search algorithm as disclosed in M. S. Bazaraa, H. D. Sherali, and C. M. Shetty, *Nonlinear programming theory and algorithms*, John Wiley & Sons Inc, New York, 1993. The Newton direction d may be required to satisfy $d^T \nabla M < 0$ (i.e., it is a descent direction for M at the point $\mu_a$). The step length $\alpha > 0$ may be chosen to guarantee that $M(\mu_a) < M(\mu_a)$, along with Wolfe's conditions disclosed in P. Wolfe, "Convergence condition for ascent method," *SIAM Rev.*, 11, 226-253, 1969, which are designed to guarantee convergence to a local minimum.

At decisional step 422, it is determined whether $\mu_a^{j+1}$ is an active variable. In general, if the variables of an unconstrained problem are very close to a bound in the inner iteration, then these variables are fixed (call active variables). Hence the start of the next unconstrained optimization uses the free variables only. The variables in $B(\mu_a)$ and $B'(\mu_a)$ are called active variables and the variables in $C(\mu_a)$ are called free variables $$B(\mu_a) = \{i : l \leq \mu_{a_i} \leq l + \epsilon\} \quad (25)$$

$$B'(\mu_a) = \{i : u - \epsilon \leq \mu_{a_i} \leq u\} \quad (26)$$

$$C(\mu_a) = \{i : l + \epsilon \leq \mu_{a_i} \leq u - \epsilon\} \quad (27)$$

where i is the number of nodal points i=1, ... n, l is the lower bound of the absorption coefficient owing to fluorophore, u is the upper bound of the absorption coefficient owing to fluorophore, and the tolerance $\epsilon$ should be sufficiently small, such that $$l + \epsilon < u - \epsilon \quad (28)$$

For example, the tolerance $\epsilon$ may be set to $10^{-3}$, $10^{-4}$, $10^{-6}$, or other suitable values. All variables in the active set are fixed during the iteration, while the other variables in set C are free. After each iteration, the active variables may be updated from current free variables, i.e., variables may be found that lie within the bounds and add to previous active variables. The active sets B and B' are updated at the inner iteration and the process is continued until the gradient of the barrier function M described by (11) can not be reduced further with the current free variables.

The variables $\mu_{a_i}$ in $C = \{\mu_{a_i} | l \leq \mu_{a_i} \leq u\}$ have three mutually exclusive possibilities:

$$(i) \quad 0 \leq \mu_{a_i} - l \leq \nabla_{\mu_{a_i}} M(\mu_a, \lambda, \eta) \quad (29)$$

$$(ii) \quad \nabla_{\mu_{a_i}} M(\mu_a, \lambda, \eta) \leq \mu_{a_i} - u \leq 0 \quad (30)$$

$$(iii) \quad \mu_{a_i} - u \leq \nabla_{\mu_{a_i}} M(\mu_a, \lambda, \eta) \leq \mu_{a_i} - l \quad (31)$$

The vector of $\mu_{a_i}$ that satisfies (i) or (ii) are now the dominated variables. The ones satisfying (i) are said to be dominated above; and those satisfying (ii) are dominated below, and those satisfying (iii) are the floating variables.

If a convergence condition is satisfied at decisional step 424, then inner stage ends and method 400 proceeds to step 430 of the outer stage. In the illustrated embodiment, the inner iteration can be considered fully converged if either of the following two conditions are satisfied. The first convergence condition is $$\left\| \frac{\nabla_{\mu_a} M(\mu_a^j, \lambda^k, \eta^k)}{1.0 + \|\mu_a^j\|} \right\| < \tau_1^k \quad (32)$$

where k is the number of the subproblem and j is the number of inner iteration. If $\tau_1^k$ is less than $10^{-5}$ then the inner iteration is stopped and the outer iteration are continued. The second convergence condition is satisfied if the fractional change $d_2$ given by (33) of the barrier function M of equation (11) of consecutive inner iterations is less than $\epsilon_0=10^{-5}$ then the inner iteration is stopped and the outer iteration are continued.

$$d_2 = \frac{|M(\mu_a^{j+1}, \lambda^k, \eta^k) - M(\mu_a^j, \lambda^k, \eta^k)|}{1.0 + |M(\mu_a^j, \lambda^k, \eta^k)|} \quad (33)$$

If neither convergence condition is satisfied at decisional step 424, then, at step 426, the inner iteration indices j is set to j+1. If the inner iteration indices j does not satisfy the specified number of inner iterations (e.g., 5, 10, etc) at decisional step 428, the inner iteration returns to step 418. Otherwise, the inner iteration ends, and execution returns to the outer iteration at step 430.

At step 430, the outer iteration indices k is set to k+1. If the outer iteration indices k satisfies the specified number of outer iterations (e.g., 6) at decisional step 432, then, at step 434, the absorption coefficient due to fluorophores $\mu_a$ is set to the current estimated value $\mu_a^{j+1}$ and execution ends. If the outer iteration indices k does not satisfy the specified number of outer iterations at decisional step 432, then execution proceeds to decision step 436. If a convergence criteria is satisfied at decisional step 436, then execution ends. The outer iteration of the PMBF can be considered fully converged if it satisfies any of the following conditions:

$$\gamma_1^{k+1} = \frac{\left\|\nabla_{\mu_a} E(\mu_a^{k+1}) - \eta^k \sum_{i=1}^n \lambda_i^k \nabla_{\mu_a} h_i(\mu_a^{k+1})\right\|}{1.0 + \|\mu_a^{k+1}\|} < \varsigma \quad (34)$$

$$\gamma_2^{k+1} = \frac{\left|\eta^k \sum_{i=1}^n \lambda_i^k \nabla_{\mu_a} h_i(\mu_a^{k+1})\right|}{1.0 + \|\mu_a^{k+1}\|} < \varsigma \quad (35)$$

where k is the number of subproblem. If $\varsigma$ is less than $10^{-5}$, then the inner iteration is stopped. If the fractional change $d_1$ given by equation (36) of the barrier function M given by equation (11) for the consecutive outer iterations is less than $\epsilon_0=10^{-5}$, then the outer iteration is stopped.

$$d_1 = \frac{|M(\mu_a^{k+1}, \lambda^{k+1}, \eta^{k+1}) - M(\mu_a^k, \lambda^k, \eta^k)|}{1.0 + |M(\mu_a^k, \lambda^k, \eta^k)|} \quad (36)$$

If the outer iteration convergence criteria are not satisfied at decisional step 436, then, at step 438, $\lambda^l$, $\lambda^u$, and $\beta$ are updated. The Lagrangian multipliers may be updated as followed:

$$\lambda^{k+1} = \begin{cases} \eta^k \lambda_i^k \left(\frac{1}{\eta^k s_i + h_i(\mu_a)}\right) & \text{for } i=1,2,\ldots,n \; h_i(\mu_a) \geq -\beta^k s_i \eta^k \\ \eta^k \lambda_i^k (q_i^1 h_i(\mu_a) + q_i^2) & \text{for } i=1,2,\ldots,n \; h_i(\mu_a) < -\beta^k s_i \eta^k \end{cases} \quad (37)$$

where $\lambda_i$ represents all the Lagrange multipliers for the bound constraints ($\lambda_i^l$ and $\lambda_i^u$) and $h_i(\mu_a)$ represents all the bound constraints. $\eta$ may be updated by a simple reduction rule:

$$\eta^{k+1} = \eta^k/\gamma \quad (38)$$

where $\gamma > 1$ is defined by the user, and normally $\gamma=2$ or $\gamma=10$, and k is the number of the outer iteration.

Next, at step 440, $\mu_{a_i}$ is updated at nodal point i, after $k^{th}$ outer iteration as follows:

$$(\hat{\mu}_a^k)_i = \begin{cases} l & \text{if } 0 \leq (\mu_a^{k-1})_i - l \leq (\nabla_{\mu_a} M^{k-1})_i \\ u & \text{if } (\nabla_{\mu_a} M^{k-1})_i \leq (\mu_a^{k-1})_i - l \leq 0 \\ (\mu_a^{k-1})_i & \text{otherwise} \end{cases} \quad (39)$$

Execution returns to step 412 to return to the inner stage.

Figure 5A:
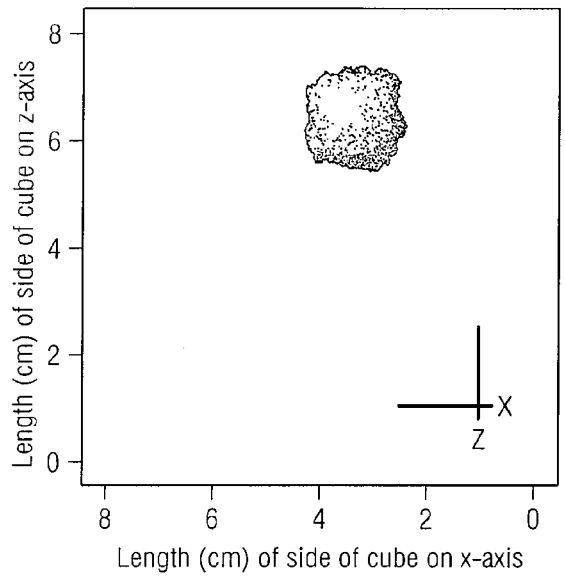
FIGS. 5A-C illustrate a reconstructed three-dimensional image of a fluorescent target.
Figure 5B:
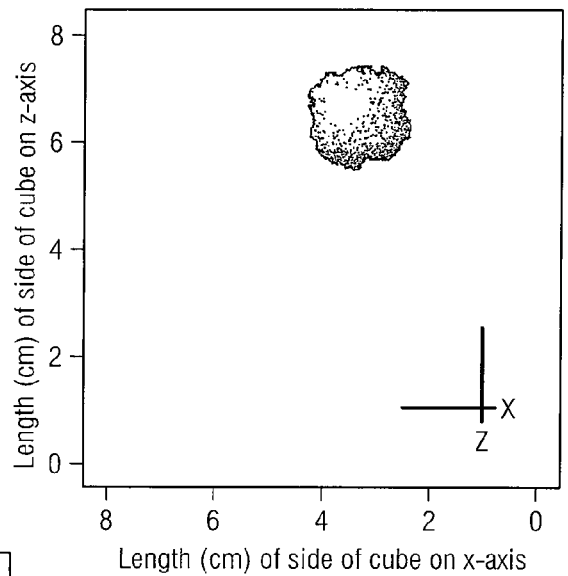
Figure 5C:
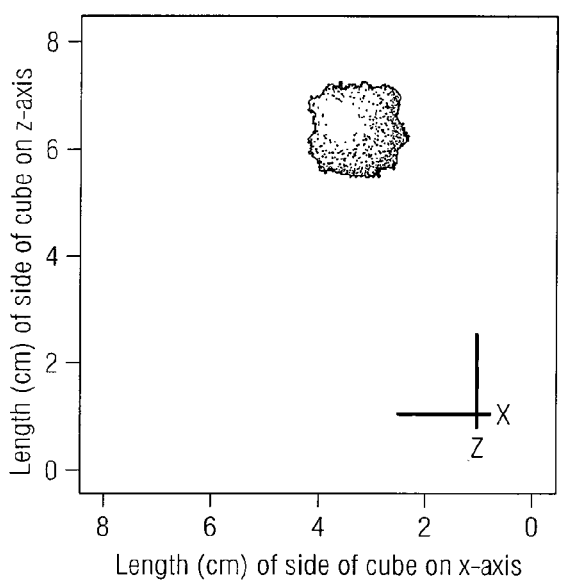

FIGS. 5A-C illustrate x-z views of a 3D distribution of a fluorescent target which provides example data generated according to the teachings of the invention. These reconstructions used the following initial values $\mu_{a_{x_i}}^0 = 0.03$ cm$^{-1}$ and $\lambda^0 = 1000$, $\mu_{a_{x_f}}^0 = 0.003$ cm$^{-1}$ and $\lambda^0 = 1000$, and $\mu_{a_{x_f}} = 0.003$ cm$^{-1}$ and $\lambda^0 = 1000$, respectively. A tissue phantom consisting of an 8×8×8 cm$^3$ cube filled with 1% lipid solution to mimic the scattering properties of tissue was used in the system of FIGS. 1 and 2. The target to be reconstructed in these initial studies was a 1 cm$^3$ cube filled with 1% lipid and 1 µM Indocyanine Green solution placed 1 cm from the imaging surface. The top surface of the tissue phantom was illuminated with an expanded beam of 785-nm excitation light which was intensity modulated at 100 MHz. The surface area illuminated was approximately 9 cm$^2$. The emitted fluorescent signal in this area was imaged using a gain modulated intensified charge coupled device (ICCD) operated under homodyne conditions to enable determination of the amplitude and phase-delay of the light emitted on the top of the surface. Using a combination crossed and parallel polarizers on the incident and collected light, the spatial distribution of the amplitude and phase delay of the incident excitation light was determined. Next upon placing an 830 nm interference and imaging holographic filters at the photocathode of the intensifier, the amplitude and phase delay of the re-emitted fluorescent light owing to the submerged target was determined across the surface of the phantom.

One advantage of this procedure is that optical fibers are not required to illuminate or collect the light signal unlike the traditional point illumination/collection measurement schemes used in optical tomography. An additional advantage of this procedure is the ability to reconstruct 3D images from data collected at a 2D sensor surface.

Although the present invention has been described in detail, various changes and modifications may be suggested to one skilled in the art. It is intended that the present invention encompass such changes and modifications as falling within the scope of the appended claims.

What is claimed is:
1. A method of imaging, comprising:
   directing time-varying excitation light at a surface area of a tissue, the tissue comprising a fluorescent target;
   modulating the intensity of the excitation light at a radio frequency;
   detecting, substantially at a two-dimensional sensor surface, time-varying emission light from the fluorescent target in response to the time-varying excitation light stimulating the fluorescent target;
   filtering the time-varying emission light to reject excitation light re-emitted from the material;
   determining a spatial distribution of amplitude and phase-delay of the detected time-varying emission light;
   detecting time-varying excitation light specularly-reflected by the fluorescent target;

determining a spatial distribution of amplitude and phase-delay of the time-varying excitation light incident on the surface area based on the reflected time-varying excitation light; and generating a three-dimensional image of the fluorescent target based on the spatial distributions of the incident time-varying excitation light and the time-varying emission light.

2. A method of imaging, comprising:

directing time-varying excitation light at a surface area of a light scattering material, the material comprising a fluorescent target;

detecting, substantially at a two-dimensional sensor surface, time-varying emission light from the fluorescent target in response to the time-varying excitation light stimulating the fluorescent target;

filtering the time-varying emission light to reject excitation light re-emitted from the material; and generating a three-dimensional image of the fluorescent target based on the detection substantially at the sensor surface.

3. The method of claim 2, wherein the fluorescent agent comprises indocyanine green ("ICG").

4. The method of claim 2, wherein the surface area is greater than 1 millimeter squared ($mm^2$).

5. The method of claim 2, further comprising determining a spatial distribution of amplitude and phase-delay of the detected time-varying emission light.

6. The method of claim 5, further comprising:

detecting time-varying excitation light specularly-reflected by the fluorescent target; and determining a spatial distribution of amplitude and phase-delay of the time-varying excitation light incident on the surface area based on the reflected time-varying excitation light.

7. The method of claim 6, wherein the three dimensional image of the fluorescent target is based on the spatial distributions of the incident time-varying excitation light and the time-varying emission light.

8. The method of claim 2, wherein the time-varying excitation light comprises a planar wave.

9. The method of claim 2, wherein the material comprises tissue.

10. The method of claim 2, further comprising modulating the intensity of the excitation light at a radio frequency.

11. The method of claim 6, wherein detecting time-varying excitation light specularly-reflected by the fluorescent target comprises:

detecting excitation light emitted from the light scattering material;

detecting multiply-scattered excitation light emitted from the light scattering material; and subtracting the detected multiply-scattered excitation light from the detected excitation light emitted from the light scattering material to determine the specularly-reflected excitation light.

12. The method of claim 2, wherein the two-dimensional sensor surface area is approximately 16 $cm^2$.

13. A system for imaging, comprising:

a laser diode operable to direct time-varying excitation light at a surface area of a light scattering material, the material comprising a fluorescent target;

an image intensifier operable to detecting, substantially at a two-dimensional sensor surface, time-varying emission light from the fluorescent target in response to the time-varying excitation light stimulating the fluorescent target;

one or more optical filters operable to filter the time-varying emission light to reject excitation light re-emitted from the material; and an imaging apparatus operable to generate a three-dimensional image of the fluorescent target based on the detection substantially at the sensor surface.

14. The system of claim 13, wherein the fluorescent agent comprises indocyanine green ("ICG").

15. The system of claim 13, wherein the surface area is approximately 9 centimeters squared ($cm^2$).

16. The system of claim 13, the imaging apparatus further operable to determine a spatial distribution of amplitude and phase-delay of the detected time-varying emission light.

17. The system of claim 13, further comprising a plurality of linear polarizers operable to pass reflected excitation light in a first configuration and multiply-reflected excitation light in a second configuration; and the image apparatus further operable to determine a spatial distribution of amplitude and phase-delay of the time-varying excitation light incident on the surface area based on the reflected and multiply-reflected excitation light.

18. The system of claim 17, wherein the three dimensional image of the fluorescent target is based on the spatial distributions of the incident time-varying excitation light and the time-varying emission light.

19. The system of claim 13, wherein the time-varying excitation light comprises a planar wave.

20. The system of claim 13, wherein the material comprises tissue.

21. The system of claim 13, wherein an intensity of the time-varying excitation light is modulated at a radio frequency.

* * * * *

UNITED STATES PATENT AND TRADEMARK OFFICE
CERTIFICATE OF CORRECTION

PATENT NO. : 7,599,732 B2  Page 1 of 1
APPLICATION NO. : 10/872333
DATED : October 6, 2009
INVENTOR(S) : Sevick-Muraca et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1313 days.

Signed and Sealed this

Twenty-eighth Day of September, 2010

David J. Kappos
*Director of the United States Patent and Trademark Office*